(12) United States Patent
Chang

(10) Patent No.: US 6,528,527 B2
(45) Date of Patent: Mar. 4, 2003

(54) METHOD OF TREATMENT WITH A COMBINATION OF A PDE4 INHIBITOR AND A LEUKOTRIENE ANTAGONIST

(75) Inventor: Yujun Chang, Doylestown, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/003,614

(22) Filed: Nov. 2, 2001

(65) Prior Publication Data

US 2002/0055520 A1 May 9, 2002

Related U.S. Application Data

(60) Provisional application No. 60/246,368, filed on Nov. 7, 2000.

(51) Int. Cl.[7] ........................ A61K 31/47; A61K 31/44
(52) U.S. Cl. ........................................ 514/311; 514/352
(58) Field of Search ................................. 514/352, 311

(56) References Cited

U.S. PATENT DOCUMENTS 5,565,473 A  * 10/1996  Belley et al. ................ 514/313
5,712,298 A  *  1/1998  Amschler .................... 514/352

OTHER PUBLICATIONS

K.F. Chung, Allergol. Int., (1998), vol. 47(4): pp. 237–246.
H.J. Dyke, et al., Expert Opinion on Investigational Drugs, (1999), vol. 8/9:pp. 1301–1325.

* cited by examiner

Primary Examiner—Raymond Henley, III
(74) Attorney, Agent, or Firm—David L. Rose

(57) ABSTRACT

Bronchial and respiratory disorders are treated by the separate, sequential, or simultaneous administration of i) an amount of N-(3,5-dichloropyrid-4-yl)-cyclopropylmethoxy-4-difluoromethoxybenzamide, the pyridyl N-oxide thereof, or a pharmaceutically acceptable salt of either compound; and ii) an amount of a leukotriene antagonist, wherein the sum of the first and second amounts is a therapeutically effective amount.

6 Claims, No Drawings

METHOD OF TREATMENT WITH A COMBINATION OF A PDE4 INHIBITOR AND A LEUKOTRIENE ANTAGONIST

CROSS-REFERENCE TO RELATED APPLICATIONS

This application claims the benefit of U.S. Provisional Application No. 60/246,368, filed on Nov. 7, 2000.

BACKGROUND OF THE INVENTION

The present invention relates to a method of treatment of bronchial and respiratory disorders with a therapeutic combination of a PDE4 inhibitor and a leukotriene antagonist. In particular, the present invention is directed to a method of treatment of bronchial and respiratory disorders with a therapeutic combination of ROFLUMILAST and SINGULAIR.

Cyclic nucleotide phosphodiesterase (PDE) inhibitors, particularly inhibitors of type IV (PDE4), are useful in the treatment of bronchial and respiratory disorders such as asthma and chronic obstuction pulminary disease (COPD). N-(3,5-dichloropyrid-4-yl)-3-cyclopropylmethoxy-4-difluoromethoxybenzamide (ROFLUMILAST, BYK Gulden Lomberg Chemische Fabrik GmbH, Konstanz, Germany) is a PDE4 inhibitor described in U.S. Pat. No. 5,712,298.

Leukotriene antagonists, by a route different from PDE4 inhibitors, are also useful in the treatment of bronchial and respiratory disorders such as asthma and COPD. Montelukast, [R-(E)]-1-[[[1-[3-[2-(7-Chloro-2-quinolinyl)ethenyl]phenyl]-3-[2-(1-hydroxy-1-methylethyl)-phenyl]propyl]thio]methyl]cyclopropaneacetic acid, (SINGULAIR, Merck & Co., Inc, Rahway, N.J.) is a leukotriene antagonist described in U.S. Pat. No. 5,565,473. Other leukotriene antagonists are described in U.S. Pat. Nos. 4,649,157, 4,845,083, 5,028,615, and 5,244,899.

It would be desirable to provide a method that can take advantage of the different therapeutic pathways of a PDE4 inhibitor and of a leukotriene antagonist to more efficaciously treat asthma and COPD.

SUMMARY OF THE INVENTION

Bronchial and respiratory disorders are treated by the separate, sequential, or simultaneous administration of i) an amount of N-(3,5-dichloropyrid-4-yl)-cyclopropylmethoxy-4-difluoromethoxybenzamide, the pyridyl N-oxide thereof, or a pharmaceutically acceptable salt of either compound; and ii) an amount of a leukotriene antagonist, wherein the sum of the first and second amounts is a therapeutically effective amount.

DETAILED DESCRIPTION OF THE INVENTION

ROFLUMILAST is a PDE4 inhibitor, N-(3,5-dichloropyrid-4-yl)-3-cyclopropylmethoxy-4-difluoromethoxybenzamide, having the following structure:

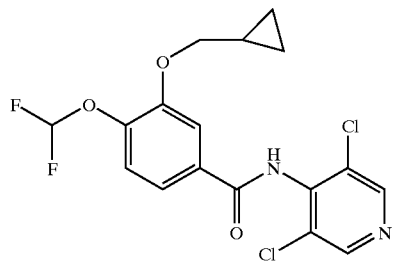

SINGULAIR is a leukotriene antagonist, Montelukast, [R-(E)]-1-[[[1-[3-[2-(7-Chloro-2-quinolinyl)ethenyl]phenyl]-3-[2-(1-hydroxy-1-methylethyl)-phenyl]propyl]thio]methyl]cyclopropaneacetic acid, having the following structure:

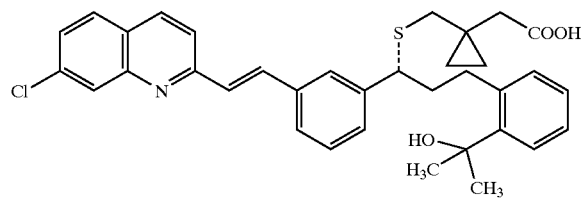

The present invention treats bronchial and respiratory disorders by adminstering a therapeutically effective amount of a combination of
  i) an amount of ROFLUMILAST, the pyridyl N-oxide thereof, or a pharmaceutically acceptable salt of either, and
  ii) an amount of a leukotriene antagonist such as SINGULAIR or a pharmaceutically acceptable salt thereof.

Because of the two unique mechanisms of action, the combination has synergistic efficacy providing better relief with fewer and milder side effects. Thus, the present invention provides a method that allows reduced dosages when compared to the individual administration of the drugs individually. The present invention also provides a method that minimizes side effects.

The present invention also provides a pharmaceutical composition comprising:
  i) an amount of ROFLUMILAST, the pyridyl N-oxide thereof, or a pharmaceutically acceptable salt of either,
  ii) an amount of a leukotriene antagonist such as SINGULAIR or a pharmaceutically acceptable salt thereof, and
  iii) a pharmaceutically acceptable carrier.

There is also provided a kit of parts comprising
  i) a first pharmaceutical composition comprising an amount of ROFLUMILAST, the pyridyl N-oxide thereof, or a pharmaceutically acceptable salt of either, and a first pharmaceutically acceptable carrier, and
  iv) a second pharmaceutical composition comprising an amount of a leukotriene antagonist such as SINGULAIR, or a pharmaceutically acceptable salt thereof, and a second pharmaceutically acceptable carrier
for simultaneous or sequential administration.

Accordingly, the present invention is directed to a method of treatment of bronchial and respiratory disorders by adminstering a therapeutically effective amount of a combination of i) an amount of ROFLUMILAST, the pyridyl N-oxide thereof, or a pharmaceutically acceptable salt of either, and ii) an amount of a leukotriene antagonist such as SINGULAIR or a pharmaceutically acceptable salt thereof.

The pharmaceutical compositions of the present invention are preferably in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums or surfactants such as sorbitan monooleate, polyethylene glycol, and other pharmaceutical diluents, e.g. water, to form a solid preformulation composition containing a homogeneous mixture of a compound of the present invention, or a pharmaceutically acceptable salt thereof.

When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of each active ingredient of the present invention. Typical unit dosage forms contain from 1 to 100 mg, for example 1, 2, 5, 10, 25, 50 or 100 mg, of each active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

For the treatment of bronchial and respiratory disorders, a suitable dosage level is about 0.01 to 250 mg/kg per day, preferably about 0.01 to 100 mg/kg per day, and especially about 0.01 to 5 mg/kg of body weight per day of each active ingredient. The compounds may be administered on a regimen of 1 to 4 times per day. In some cases, however, dosage outside these limits may be used.

The synergistic effect of the combination of the present invention can be shown, for example, by comparing the combined dosage of the combination with dosages of the same amount of each of the active ingredients separately on subjects using assays such as the Asthmatic Rat Assay, PAF-Induced Hyperalgesia Assay, the Pulmonary Mechanics in Trained Conscious Squirrel Monkeys, and the Prevention of Induced Bronchoconstriction in Allergic Sheep, as described in U.S. Pat. Nos. 4,845,083 and 5,565,473.

What is claimed is:

1. (Amended) A composition comprising a synergistic combination of i) N-(3,5-dichloropyrid-4-yl)-cyclopropylmethoxy-4-difluoromethoxybenzamide, the pyridyl N-oxide thereof, or a pharmaceutically acceptable salt of either compound; and ii) a leukotriene antagonist.

2. The composition according to claim 1 wherein said leukotriene antagonist is [R-(E)]-1-[[[1-[3-[2-(7-chloro-2-quinolinyl)ethenyl]phenyl]-3-[2-(1-hydroxy-1-methylethyl)-phenyl]propyl]thio]methyl] cyclopropaneacetic acid or a pharmaceutically acceptable salt thereof.

3. The composition according to claim 2 wherein said leukotriene is [R-(E)]-1-[[[1-[3-[2-(7-chloro-2-quinolinyl)ethenyl]phenyl]-3-[2-(1-hydroxy-1-methylethyl)-phenyl]propyl]thio]methyl]cyclopropaneacetic acid, monosodium salt.

4. A method of treatment of bronchial and respiratory disorders comprising:

administering a therapeutically effective amount of a composition according to claim 1.

5. A method of treatment according to claim 4 wherein said disorders are asthma and COPD.

6. (Amended) A method of treatment of bronchial and respiratory disorders comprising the separate, sequential, or simultaneous administration of i) a first amount of N-(3,5-dichloropyrid-4-yl)-cyclopropylmethoxy-4-difluoromethoxybenzamide, the pyridyl N-oxide thereof, or a pharmaceutically acceptable salt of either compound; and ii) a second amount of a leukotriene antagonist, wherein the sum of the first and second amounts is a therapeutically synergistic effective amount.

* * * * *